United States Patent [19]

Kameoka et al.

[11] Patent Number: 5,166,375

[45] Date of Patent: Nov. 24, 1992

[54] ANTIOXIDANT AND AN OXIDATION RESISTANT POLYUNSATURATED OIL

[75] Inventors: Hiromu Kameoka, Sennan; Kiyoshi Furukawa, Osaka; Hiroshi Kihara, Musashino; Atsuyoshi Nishina, Omiya, all of Japan

[73] Assignees: Nippon Oil and Fats Company, Limited, Tokyo; Nagaoka Perfumery Company, Limited, Osaka, both of Japan

[21] Appl. No.: 741,892

[22] Filed: Aug. 8, 1991

[30] Foreign Application Priority Data

Aug. 9, 1990 [JP] Japan .................................. 2-210647
Aug. 9, 1990 [JP] Japan .................................. 2-210648

[51] Int. Cl.$^5$ .......................... C11B 5/00; C07C 51/50
[52] U.S. Cl. .......................................... 554/2; 554/3; 252/8; 252/9; 252/397; 252/407; 549/408; 568/328; 568/335; 568/337
[58] Field of Search .................... 260/398.5; 554/2, 3; 252/397, 8, 9, 407; 549/408; 568/328, 335, 337

[56] References Cited

PUBLICATIONS

Chemical Abstracts, vol. 111, #10, p. 378, 1988, 83870t (Ikeda et al.).
Chemical Abstracts, vol. 111, #20, p. 420, 1989, 239556h.
Chemical Abstracts, vol. 105, #9, p. 550, 1986, 77811j.

Primary Examiner—Jose G. Dees
Assistant Examiner—Deborah D. Carr
Attorney, Agent, or Firm—Millen, White, Zelano and Branigan

[57] ABSTRACT

The antioxidant is safe for human health, has excellent antioxidation activity and is suitably utilized for preventing oxidation of unsaturated fatty acids, esters of unsaturated fatty acids and various kinds of products comprising these acids and esters. The oxidation resistant polyunsaturated oil is made by giving strong antioxidation activity to polyunsaturated oils, such as polyunsaturated fatty acids, esters of polyunsaturated fatty acids and polyunsaturated fats.

The antioxidant comprises musizin and tocopherol as the effective components. The oxidation resistant polyunsaturated oil and fat of the invention is characterized in that an antioxidant comprising musizin as the effective component is added to a polyunsaturated oil.

9 Claims, No Drawings

ANTIOXIDANT AND AN OXIDATION RESISTANT POLYUNSATURATED OIL

BACKGROUND OF THE INVENTION

1. Field of the Invention

The present invention relates to a novel antioxidant and a novel oxidation resistant polyunsaturated oil comprising the antioxidant. More particularly, the present invention relates to a novel antioxidant which is safe for human health, excellent in the antioxidation effect and particularly suitable for preventing oxidation of unsaturated fatty acids, esters of unsaturated fatty acids and various products comprising these acids and esters. The present invention also relates to a novel oxidation resistant polyunsaturated oil which is made by giving strong antioxidation activity to eicosapentaenoic acid, docosahexaenoic acid, esters of these acids or fats comprising eicosapentaenoic acid or docosahexaenoic acid as the fatty acid component by addition of an antioxidant comprising musizin as the effective component.

2. Description of the Prior Art

Antioxidants are generally utilized for oil, fats and products containing oil and fats for the purpose of preventing change of smell, taste and color by rancidity. Examples of such generally utilized antioxidants are synthetic antioxidants, such as butylhydroxyanisole (BHA) and butylhydroxytoluene (BHT), and natural antioxidants, such as tocopherol, L-ascorbic acid, citric acid, melanoidin, flavonoids, amino acids, phitic acid and gallic acid.

However, the synthetic antioxidants such as BHA and BHT are not always safe for human health even though they are less expensive and excellent in the antioxidation effect and application of them to foods are being considered to have problems. On the other hand, the natural antioxidants do not have sufficient antioxidation effect even though they are safe for human health. Thus, the generally utilized antioxidants have a disadvantage while they have an advantage. Development of novel antioxidants having the excellent antioxidation effect and the safety for human health simultaneously has been strongly desired.

Recently, polyunsaturated fatty acids, such as eicosapentaenoic acid and docosahexaenoic acid, are attracting attention because of their useful physiological effect, such as suppression of coagulation of blood platelet, depression of neutral fats in blood, depression of cholesterol in blood, depression of viscosity of blood, antitumor activity and the like, and being utilized for functional foods, food additives, medicines, toiletries, feed stuffs and like others.

However, the polyunsaturated fatty acids of this kind are usually contained in fish oils. Because they are oxidized very rapidly and the mechanism of the oxidation is different from oxidation of fats and oils of land animals and plants, the oxidation can not be effectively prevented by the generally utilized antioxidants described above.

Musizin which is a naphthalenic compound has been known to have antioxidation effect (Laid Open Japanese Patent Publication Showa 61-66787). However, synergistic effect of musizin with other antioxidants has not been known and no example of utilization of synergistic effect of musizin and tocopherol has been published.

Antioxidation activity of musizin against polyunsaturated fatty acids and polyunsaturated oils and fats containing polyunsaturated fatty acids as the fatty acid components has not been known at all and no example of utilization of musizin for polyunsaturated fatty acids and polyunsaturated oils and fats has been published.

SUMMARY OF THE INVENTION

The present invention accordingly has an object to provide a novel antioxidant which is safe for human health, has excellent antioxidation effect and is suitably utilized for preventing oxidation of unsaturated fatty acids, esters of unsaturated fatty acids and various kinds of products comprising these acids and esters.

Another object of the present invention is to provide an oxidation resistant polyunsaturated oil which is made by giving strong antioxidation activity to polyunsaturated oils, such as polyunsaturated fatty acids, esters of polyunsaturated fatty acids and polyunsaturated fats.

Thus, the antioxidant of the invention comprises the component (A) which is musizin and the component (B) which is tocopherol as the effective components.

The oxidation resistant polyunsaturated oil of the invention is characterized in that an antioxidant comprising the component (A) which is musizin as the effective component is added to a polyunsaturated oil.

Other and further objects, features and advantages of the invention will appear more fully from the following description.

DESCRIPTION OF THE PREFERRED EMBODIMENTS

Investigations to achieve the above objects were made extensively by the present inventors and it was discovered that the combination of musizin and tocopherol is safe for human health, has excellent effect of preventing oxidation by the synergistic effect of the components and can be utilized to achieve the objects, thus leading to the completion of the invention.

Furthermore, investigations were made also to develop an oxidation resistant polyunsaturated oil having excellent antioxidation activity and it was discovered that the above object can be achieved by adding an antioxidant comprising musizin as the effective component to polyunsaturated oils, thus leading to the completion of the invention.

The present invention provides an antioxidant comprising the component (A) which is musizin and the component (B) which is tocopherol as the effective components. The present invention also provides an oxidation resistant polyunsaturated oil which is characterized in that an antioxidant comprising the component (A) which is musizin as the effective component is added to a polyunsaturated oil.

The invention is explained in detail in the following.

Musizin which is the component (A) of the effective components in the antioxidant of the invention is a derivative of β-methylnaphthalene shown by the general formula:

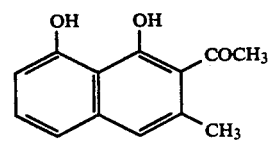

Musizin may be prepared by synthesis according to generally known methods or obtained by extraction from natural products.

When musizin is extracted from natural products, musizin is contained in plants of Polygonaceae, such as Rumex japonicus like Rumex japonicus Houtt and Rumex conglomeratus Murr. Whole plants or roots of these plants are treated with extraction by a suitable solvent, such as an aliphatic hydrocarbon or an alicyclic hydrocarbon like n-hexane, n-pentane, cyclohexane and the like, a lower alcohol like methanol, ethanol and the like, an ether like diethyl ether, tetrahydrofuran and the like, a halogenated hydrocarbon like dichloroethane, ethylene dichloride and the like and an aromatic hydrocarbon like benzene, toluene and the like and the solvent is removed by distillation. The extract may be, according to needs, further purified by a suitable method, such as treatment with alkali, chromatography, recrystallization and the like methods.

The plants containing musizin described above have been utilized as materials for crude drugs for a long time and the toxicity of musizin can be considered to be very low. Thus, musizin can be considered to be safe for human health.

Tocopherol which is utilized as the other component (B) of the effective components in the antioxidant of the invention is a member of a group of fat soluble vitamins which were discovered as an antisterility factor contained in plants and form a group of vitamin E derivatives having the general formula:

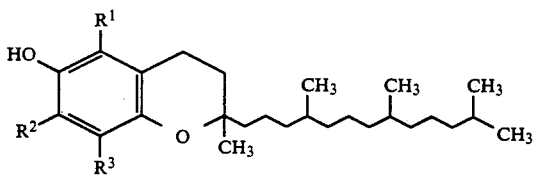

wherein $R^1$, $R^2$ and $R^3$ are a hydrogen atom or methyl group, respectively. There are four types of natural tocopherol which are $\alpha$-, $\beta$-, $\gamma$- and $\delta$-types. Hydrogen atoms of the cumarone ring are partially substituted by methyl groups and the positions of the substitution are different according to the type as shown in Table 1.

Any types of tocopherol can be utilized in the invention. Tocopherols of mixed types in which tocopherols of various types are mixed, such as a condensed natural tocopherol, are preferably utilized. Tocopherols of this kind are available commercially. A single kind of commercial tocopherol may be utilized as served or two or more kinds of commercial tocopherol may be utilized as a mixture. Tocopherol may be utilized in a form diluted with oil or fat. Synthetic D,L-α-tocopherol prepared from 2,3,5-trimethylhydroquinone and isophitol may utilized as the tocopherol of the component (B).

In the antioxidant of the invention, musizin of the component (A) and tocopherol of the component (B) are comprised in a weight ratio in the range from 1:9 to 9:1, preferably in the range from 4:6 to 6:4 and more preferably in the range from 4.5:5.5 to 5.5:4.5. When the components are comprised in an weight ratio outside of the range described here, the desired synergistic effect may be lacking and the object of the invention may be left unattained.

When gallic acid is added to the antioxidant of the invention, the antioxidation effect is further enhanced. The amount of gallic acid utilized is not particularly limited but is generally in the range from 5 to 95 weight parts and preferably in the range from 10 to 50 weight parts per 100 weight parts of the total of the component (A) and the component (B).

One or more kinds of other ingredients having antioxidation activity and safe for human health, such as L-ascorbic acid, citric acid, melanoidin, flavonoids, amino acids, phitic acid and the like, may be comprised in the antioxidant of the invention according to desire so long as the ingredients do not make harm to the object of the invention.

Form of the antioxidant of the invention in application is not particularly limited but the antioxidant can be formed into any kind of formulation, such as powder, granule, emulsion, solution, suspension and the like others. When the antioxidant is formed into a formulation, solid carriers and liquid carriers which are generally utilized in foods and toiletries, surface active agents, emulsifiers, suspension agents and the like may be utilized according to necessity.

When, for example, the antioxidant is utilized in the form of solution, it may be diluted by a liquid carrier, such as food oil, ethanol and the like. When the antioxidant is insoluble in the material to be utilized, it may be formed into O/W type emulsion by emulsifying with water by using a suitable emulsifier such as glycerol ester of a fatty acid and then added to the material.

The antioxidant is favorably utilized in products in which prevention of oxidation is required. Examples of such products are food oils, milk products, margine, shortenings, lard, meat products, canned products, fish products, instant foods, cookies, drinks like refreshing drinks, health foods, medicines, toiletries such as cream, lotion, emulsion, sun oil, lanolin, soap and the like, and the like other products. The antioxidant of the invention is particularly favorably utilized in unsaturated acids, esters of unsaturated acids and products containing such acids and esters.

The antioxidant is utilized generally in the amount in the range from 10 to 1,000 ppm for ordinary oils and fats containing rather low unsaturation and generally in the range from 100 to 10,000 ppm, preferably in the range from 100 to 1,000 ppm and more preferably in the range from 500 to 1,000 ppm for polyunsaturated oils.

However, the amount of the antioxidant utilized in the invention is not particularly limited but suitably selected according to the material which needs prevention of oxidation. When the amount is less than 10 ppm, the antioxidation effect may be insufficient. When the amount is more than 10,000 ppm, the antioxidation effect is not so much enhanced as expected from the amount utilized and rather disadvantageous from economic point of view. Thus, amounts outside of the range is not preferable.

When the antioxidant is utilized for materials of powder form, such as fish meal, the amount in the range from 1,000 to 10,000 ppm is required for having sufficient antioxidation effect. For application of the antioxidant for foods, it is necessary to adjust the amount of the antioxidant according to the shape, the content of oils and fats and other related factors.

The polyunsaturated oil to which the antioxidant of the invention comprising musizin as the effective component is added is a polyunsaturated fatty acid, an ester of the polyunsaturated fatty acid and a polyunsaturated fat comprising the polyunsaturated fatty acid as the fatty acid component. Examples of the polyunsaturated oil are at least one kind selected from the group consisting of eicosapentaenoic acid, docosahexaenoic acid, an ester of eicosapentaenoic acid and an ester of docosahexaenoic acid and a polyunsaturated fat comprising eicosapentaenoic acid and/or docosahexaenoic acid as the fatty acid component. Preferable examples of the polyunsaturated oil are fish oil and like other oils.

The amount of the antioxidant comprising musizin as the effective component utilized in the polyunsaturated oil is generally in the range from 100 to 10,000 ppm, preferably in the range from 100 to 1,000 ppm and more preferably in the range from 500 to 1,000 ppm based on the polyunsaturated oil. When the amount utilized is less than 10 ppm, the antioxidation effect may be insufficient depending upon the condition of service. When the amount utilized is more than 10,000 ppm, unfavorable things, such as coloring of the product, may take place.

The oxidation resistant polyunsaturated oil of the invention can comprise, according to desire, other generally known antioxidants along with musizin as components of the antioxidant comprising musizin as the effective component. Examples of such generally known antioxidants are natural antioxidants, such as tocopherol, ascorbic acid, gallic acid and the like, and synthetic antioxidants, such as butylhydroxyanisol, butylhydroxytoluene and the like. Preferable generally known antioxidants are tocopherol and gallic acid. Particularly preferable generally known antioxidant is tocopherol. The amount of the generally known antioxidant utilized is generally in the range from 1 to 1,000 weight % based on the weight of musizin.

The invention will be understood more readily with reference to the following examples; however these examples are intended to illustrate the invention and are not to be construed to limit the scope of the invention.

Evaluation of Peroxide Value

Peroxide value which is used in examples as the measure of antioxidation activity is expressed by milliequivalent of iodine isolated by addition of potassium iodide to a sample per one kilogram of the sample according to the method of measurement specified by the Society of Oil and Fat Chemistry of Japan.

The method of measurement of the peroxide value is as following: a definite amount of a sample is weighed into an Erlenmeyer flask with a glass stopper, 35 ml of a solvent is added to the flask and the mixture is quietly shaken until the sample is dissolved to form a clear solution. The air inside of the flask is replaced by pure nitrogen by passing pure nitrogen gas through the flask. After exactly 1 ml of a solution of potassium iodide is added to the solution while the nitrogen is being passed through the flask, the flow of nitrogen is stopped and the glass stopper is immediately fitted into the flask. The flask is shaken for 1 minute and left standing for 5 minutes in a dark place of the room temperature. After standing for 5 minutes, 75 ml of water is added to the flask, the stopper is fitted into the flask and the flask is vigorously shaken. The solution in the flask is titrated with N/100 standard solution of sodium thiosulfate by using a solution of starch as the indicator. When the color by the starch disappears, the titration is finished. The peroxide value is calculated by the following equation:

Peroxide value $= (A \times F/B) \times 10$ where A is the amount in ml of N/100 standard solution of sodium thiosulfate used for the titration, F is the potency of the N/100 standard solution of sodium thiosulfate and B is the amount of the sample utilized for the measurement.

EXAMPLE OF PREPARATION OF ANTIOXIDANT 1

To 1 kg of Rumex japonicus Hutt, grown in Wakayama Prefecture, Japan, which was lipophilized, 5 kg of n-hexane was added and left standing for a whole day. The extract solution was filtered and 15 g of an extract was obtained after removing n-hexane by distillation with an evaporator. The content of musizin in the extract which was measured by using a high performance liquid chromatography apparatus (a product of Shimadzu Corporation, LC-5A) was about 50 weight %.

EXAMPLE OF PREPARATION OF ANTIOXIDANT 2

The extract prepared in the Example of preparation of antioxidant 1, 1 g, was treated with a silica gel column chromatography. n-Hexane, ether, ethyl acetate, chloroform and methanol were used as the solvent for elution successively. The solution obtained by elution with chloroform was concentrated and the substance contained was recrystallized. The content of musizin in the recrystallized substance which was measured by using a high performance liquid chromatography apparatus (a product of Shimadzu Corporation, LC-5A) was about 90 weight %.

EXAMPLE 1

To a commercial methyl linolate, 0.1 weight % of a mixture of musizin and γ-tocopherol in a weight ratio of 1:90 was added and the mixture methyl linolate was kept at 50° C. Change of weight of the mixture of methyl linolate was measured periodically and the period of time until the weight showed rapid increase (the induction period in days) was obtained. The antioxidation effect was evaluated by the value of the induction period. The results are shown in Table 2.

EXAMPLES 2 THROUGH 4 AND COMPARATIVE EXAMPLES 1 THROUGH 3

The antioxidant activity of various mixtures were evaluated in the same method as in Example 1 except that a compound or a mixture shown in Table 2 were utilized as the antioxidant in place of the mixture of 10:90 mixture of musizin and tocopherol. The results are shown in Table 2.

COMPARATIVE EXAMPLE 4

The antioxidant activity of a mixture was evaluated in the same method as in Example 1 except that no antioxidant was utilized. The result is shown in Table 2.

EXAMPLE 5

To a freshly prepared fish meal made from sardine as the material, 1 weight % of a mixture of musizin and a mixed tocopherol (a product of Eisai Co., Ltd., E-mix 80 ®) in a weight ratio of 10:90 was added and the mixture was mixed sufficiently. Then, the mixture was placed in a constant temperature oven at 50° C. and the period of time until the peroxide value reached to 100 was measured. The antioxidation effect was evaluated by the period in days. The result is shown in Table 3.

E-mix 80 ® contains 5 weight % of α-tocopherol, 60 weight % of γ-tocopherol and 35 weight % of δ-tocopherol.

EXAMPLES 6 THROUGH 8 AND COMPARATIVE EXAMPLES 5 THROUGH 7

The antioxidation effect of various mixtures were evaluated in the same method as in Example 4 except that a compound or a mixture shown in Table 3 were utilized as the antioxidant in place of the 10:90 mixture of musizin and the mixed tocopherol. The results are shown in Table 3.

COMPARATIVE EXAMPLE 8

The antioxidation effect of a mixture was evaluated in the same method as in Example 4 except that no antioxidant was utilized. The result is shown in Table 3.

EXAMPLE 9

To a commercial purified lard, 50 ppm of a mixture of musizin and a mixed tocopherol (a product of Eisai Co., Ltd., Eamix 80 ®) in a weight ratio of 10:90 was added and the mixture was mixed sufficiently. Then, the mixture was placed in a thermostatted vessel at 50° C. and the period of time until the peroxide value reached to 100 was measured. The antioxidation effect was evaluated by the period in days. The result is shown in Table 4.

EXAMPLES 10 THROUGH 12 AND COMPARATIVE EXAMPLES 9 THROUGH 11

The antioxidation effect of various mixtures were evaluated in the same method as in Example 7 except that a compound or a mixture shown in Table 4 were utilized as the antioxidant in place of the mixture of 10:90 mixture of musizin and the mixed tocopherol. The results are shown in Table 4.

COMPARATIVE EXAMPLE 12

The antioxidation effect of a mixture was evaluated in the same method as in Example 7 except that no antioxidant was utilized. The result is shown in Table 4.

Examples 1 through 12 in which the antioxidants of the invention were utilized showed clearly better antioxidation effects when they are compared with Comparative examples 4, 8 and 12 in which no antioxidant was utilized and with Comparative examples 1, 2, 3, 5, 6, 7, 9, 10 and 11 in which a natural antioxidant was utilized alone, as clearly shown in Tables 2, 3 and 4.

EXAMPLE 13

To a commercial fish oil (a product of Nippon Oil and Fats Co., Ltd.), an antioxidant shown in Table 5 was added in an amount of 0.05 weight % in every case and the mixture was kept at 60° C.

Weight of the mixtures did not change remarkably during the initial period of the oxidation but made rapid increase after certain stage of the oxidation. The change of the weight was measured and the period before the rapid increase of the weight (the induction period in days) was obtained to evaluate the antioxidation effect. The results are shown in Table 5.

EXAMPLE 14

To a commercial ethyl eicosapentaenoate (a product of Nippon Oil and Fats Co., Ltd.), 0.1 weight % of an antioxidant shown in Table 6 was added in every case and the antioxidation effect was evaluated by using Ransimat ® (a product of Metrome Co., Ltd.) at 120° C. The antioxidation effect was evaluated by measuring induction period. The result is shown in Table 6.

EXAMPLE 15

To a freshly prepared fish meal made from sardine as the material, 1 weight % of an antioxidant shown in Table 7 was added in every case and the mixture was mixed sufficiently. Then, the mixture was placed in a thermostatted vessel at 50° C. and the period of time until the peroxide value reached to 100 was measured. The antioxidation effect was evaluated by the period in days. The result is shown in Table 7.

COMPARATIVE EXAMPLE 13

To a commercial lard (a product of Nippon Oil and Fats Co., Ltd.), 0.1 weight % of an antioxidant shown in Table 8 was added in every case and the mixture was kept in a thermostatted vessel at 60° C. The change of the weight was measured and the period before the rapid increase of the weight (the induction period in days) was obtained to evaluate the antioxidation effect. The result is shown in Table 8.

COMPARATIVE EXAMPLE 14

To a commerical purified soy bean oil (a product of Nippon Oil and Fats Co., Ltd.), 0.02 weight % of an antioxidant shown in Table 9 was added in every case and the mixture was kept at 60° C. The change of the weight was measured and the period before the rapid increase of the weight (the induction period in days) was obtained to evaluate the antioxidation effect. The result is shown in Table 9.

The results in Tables 8 and 9 show that the antioxidation effects of musizin in lard and in soy bean oil are rather slight. On the other hand, musizin has a high degree of antioxidation activity in fish oils which are polyunsaturated fats, fish meals which contain the fish oil and ethyl eicosapentaenoate which is an ester of a polyunsaturated fatty acid.

While the invention has been particularly shown and described with reference to preferred embodiments thereof, it will be understood by those skilled in the art that the foregoing and other changes in form and details can be made therein without departing from the spirit and scope of the invention.

To summarize the advantages obtained by the invention, the antioxidant of the invention comprises a combination of musizin and tocopherol, is safe for human health, have much stronger antioxidation activity than natural antioxidants by synergistic effect of the components and is favorably utilized for prevention of oxidation in drinks, healthy foods, medicines, toiletries and the like others.

The polyunsaturated oil of the invention has much more excellent antioxidation activity than oils containing conventional natural antioxidants by the effect of musizin comprised in the polyunsaturated oil, such as a polyunsaturated fatty acid, an ester of polyunsaturated fatty acid and a polyunsaturated fat. Because musizin is safe for human health, the polyunsaturated oil comprising musizin is also safe for human health.

TABLE 1

| tocopherol | $R^1$ | $R^2$ | $R^3$ |
|---|---|---|---|
| α-type | $CH_3$ | $CH_3$ | $CH_3$ |
| β-type | $CH_3$ | H | $CH_3$ |
| γ-type | H | $CH_3$ | $CH_3$ |
| δ-type | H | H | $CH_3$ |

TABLE 2

| | antioxidant | induction period, days |
|---|---|---|
| Example 1 | 10:90 (weight) mixture of musizin and γ-tocopherol | 5.0 |
| Example 2 | 50:50 (weight) mixture of musizin and γ-tocopherol | 8.0 |
| Example 3 | 80:20 (weight) mixture of musizin and γ-tocopherol | 5.0 |
| Example 4 | 5:80:15 (weight) mixture of musizin, γ-tocopherol and gallic acid | 7.5 |
| Comparative example 1 | L-ascorbic acid | 1.5 |
| Comparative example 2 | γ-tocopherol | 2.0 |
| Comparative example 3 | musizin | 2.5 |
| Comparative example 4 | none | 1.0 |

TABLE 3

| | antioxidant | period of time to 100 peroxide value, days |
|---|---|---|
| Example 5 | 10:90 (weight) mixture of musizin and mixed tocopherol | 18 |
| Example 6 | 50:50 (weight) mixture of musizin and mixed tocopherol | 22 |
| Example 7 | 80:20 (weight) mixture of musizin and mixed tocopherol | 17 |
| Example 8 | 5:80:15 (weight) mixture of musizin, mixed tocopherol and gallic acid | 19 |
| Comparative example 5 | L-ascorbic acid | 3 |
| Comparative example 6 | mixed tocopherol[1] | 5 |
| Comparative example 7 | musizin | 7 |
| Comparative example 8 | none | 2 |

[1] E-mix 80 ® containing 5 weight % of α-tocopherol, 60 weight % of γ-tocopherol and 35 weight % of δ-tocopherol.

TABLE 4

| | antioxidant | period of time to 100 peroxide value, days |
|---|---|---|
| Example 9 | 10:90 (weight) mixture of musizin and mixed tocopherol | 20 |
| Example 10 | 50:50 (weight) mixture of musizin and mixed tocopherol | 28 |
| Example 11 | 80:20 (weight) mixture of musizin and mixed tocopherol | 21 |
| Example 12 | 5:80:15 (weight) mixture of musizin, mixed tocopherol and gallic acid | 25 |
| Comparative example 9 | L-ascorbic acid | 5 |
| Comparative example 10 | mixed tocopherol[1] | 6 |
| Comparative example 11 | musizin | 8 |
| Comparative example 12 | none | 4 |

[1] the same as in Table 3.

TABLE 5

| antioxidant | induction period, days |
|---|---|
| none | 1.0 |
| L-ascorbic acid | 1.0 |
| mixed tocopherol[1] | 2.0 |
| gallic acid | 2.0 |
| the extract of Example of preparation of antioxidant 1 | 6.5 |
| the purified extract of Example of preparation of antioxidant 2 | 8.0 |

[1] the same as in Table 3.

TABLE 6

| antioxidant | induction period, hours |
|---|---|
| none | 2 |
| L-ascorbic acid | 3 |
| mixed tocopherol[1] | 8 |
| the extract of Example of preparation of antioxidant 1 | 35 |
| the purified extract of Example of preparation of antioxidant 2 | 39 |
| 50:50 (weight) mixture of the extract of Example of preparation of antioxidant 1 and tocopherol | 49 |
| 50:50 (weight) mixture of the purified extract of Example of preparation of antioxidant 2 and gallic acid | 46 |

[1] the same as in Table 3.

TABLE 7

| antioxidant | period of time to 100 peroxide value, days |
|---|---|
| none | 3 |
| L-ascorbic acid | 4 |
| mixed tocopherol[1] | 9 |
| the extract of Example of preparation of antioxidant 1 | 16 |
| the purified extract of Example of preparation of antioxidant 2 | 19 |
| 50:50 (weight) mixture of the extract of Example of preparation of antioxidant 1 and tocopherol | 22 |
| 50:50 (weight) mixture of the purified extract of Example of preparation of antioxidant 2 and gallic acid | 21 |

[1] the same as in Table 3.

TABLE 8

| antioxidant | induction period, days |
|---|---|
| none | 1.0 |
| L-ascorbic acid | 1.5 |
| mixed tocopherol[1] | 4.0 |
| gallic acid | 5.5 |
| the extract of Example of preparation of antioxidant 1 | 1.5 |
| the purified extract of Example of preparation of antioxidant 2 | 1.5 |

[1] the same as in Table 3.

TABLE 9

| antioxidant | induction period, days |
|---|---|
| none | 3.0 |
| L-ascorbic acid | 4.5 |
| mixed tocopherol[1] | 6.0 |
| gallic acid | 7.0 |
| the extract of Example of preparation of antioxidant 1 | 3.5 |
| the purified extract of Example of preparation | 4.0 |

TABLE 9-continued

| antioxidant | induction period, days |
|---|---|
| of antioxidant 2 | |

1) the same as in Table 3.

What is claimed is:

1. A polyunsaturated oil rendered oxidation resistant by the presence therein of an antioxidant effective amount of musizin having the formula:

[Structure: naphthalene with OH, OH, COCH₃, CH₃ substituents]

2. An oxidation resistant polyunsaturated oil as claimed in claim 1, wherein the polyunsaturated oil is at least one compound selected from the group consisting of eicosapentaenoic acid, docosahexaenoic acid, esters of eicosapentaenoic acid and esters of docosahexaenoic acid.

3. An oxidation resistant polyunsaturated oil as claimed in claim 1, wherein the polyunsaturated oil is a polyunsaturated fat comprising eicosapentaenoic acid and/or docosahexaenoic acid as the fatty acid component.

4. An oxidation resistant polyunsaturated oil as claimed in claim 1, comprising from 100 to 10,000 ppm based on the polyunsaturated oil of the antioxidant.

5. An oxidation resistant polyunsaturated oil as claimed in claim 1, comprising from 100 to 1,000 ppm based on the polyunsaturated oil of the antioxidant.

6. An oxidation resistant polyunsaturated oil as claimed in claim 3, comprising from 500 to 1,000 ppm based on the polyunsaturated oil of the antioxidant.

7. An antioxidant composition comprising component (A) which is musizin having the formula:

[Structure: naphthalene with OH, OH, COCH₃, CH₃ substituents]

and component (B) which is tocopherol having the formula:

[Structure: chromanol with $R^1$, $R^2$, $R^3$ substituents and phytyl side chain with CH₃ groups]

wherein $R^1$, $R^2$ and $R^3$ each is a hydrogen atom or a methyl group, as the effective components in a weight ratio of component (A) to component (B) of from 4:6 to 6:4.

8. An antioxidant composition as claimed in claim 1, further comprising gallic acid.

9. An antioxidant composition as claimed in claim 1 wherein the amount of gallic acid is 10 to 50 weight parts per 100 weight parts of component (A) and (B).

* * * * *